(12) United States Patent
Hashimoto et al.

(10) Patent No.: US 8,183,429 B2
(45) Date of Patent: May 22, 2012

(54) COMPOSITE SHEET AND ABSORBENT ARTICLE COMPRISING COMPOSITE SHEET

(75) Inventors: Tatsuya Hashimoto, Kagawa (JP); Hirotomo Mukai, Kagawa (JP); Satoshi Mitsuno, Kagawa (JP); Tomoko Tsuji, Kagawa (JP); Kenichi Akaki, Kagawa (JP)

(73) Assignee: Uni-Charm Corporation, Ehime (JP)

( * ) Notice: Subject to any disclaimer, the term of this patent is extended or adjusted under 35 U.S.C. 154(b) by 413 days.

(21) Appl. No.: 12/516,135

(22) PCT Filed: Nov. 26, 2007

(86) PCT No.: PCT/JP2007/072786
§ 371 (c)(1),
(2), (4) Date: May 22, 2009

(87) PCT Pub. No.: WO2008/066010
PCT Pub. Date: Jun. 5, 2008

(65) Prior Publication Data
US 2010/0049153 A1 Feb. 25, 2010

(30) Foreign Application Priority Data

Nov. 28, 2006 (JP) ................. 2006-319596

(51) Int. Cl.
*A61F 13/15* (2006.01)
(52) U.S. Cl. ........ 604/370; 604/367; 604/366; 604/373; 604/378; 604/380; 604/384
(58) Field of Classification Search .................. 604/370, 604/367, 366, 373, 378, 380, 385.01, 384
See application file for complete search history.

(56) References Cited

U.S. PATENT DOCUMENTS

| 4,652,487 A | 3/1987 | Morman |
| 4,657,802 A | 4/1987 | Morman |
| 2004/0005832 A1* | 1/2004 | Neculescu et al. ............ 442/149 |
| 2006/0121812 A1 | 6/2006 | Suzuki et al. |

(Continued)

FOREIGN PATENT DOCUMENTS

EP 0212284 3/1987

(Continued)

OTHER PUBLICATIONS

International Search Report of Application No. PCT/JP2007/072786 mailed Feb. 19, 2008.

(Continued)

*Primary Examiner* — Jacqueline F. Stephens
(74) *Attorney, Agent, or Firm* — Lowe, Hauptman, Ham & Berner, LLP

(57) ABSTRACT

A composite sheet which has a low basis weight, can be prevented from breaking during the production of an absorbent article or in use, and is good to the touch. The composite sheet is a sheet formed by bonding a stretch nonwoven fabric to a nonstretch nonwoven fabric with an adhesive. The stretch nonwoven fabric is bonded in a stretched state to the nonstretch sheet. The stretch nonwoven fabric has, on each side, strip-form sparse regions and strip-form dense regions alternately formed. The sparse regions and dense regions on one side are alternately formed in a second direction so that the dense regions on this side do not overlie the dense regions on the other side. The composite sheet has a maximum breaking strength of 20 N/50 mm or higher.

13 Claims, 10 Drawing Sheets

U.S. PATENT DOCUMENTS

2006/0141883 A1  6/2006  Nishiguchi et al.

FOREIGN PATENT DOCUMENTS

| | | | |
|---|---|---|---|
| EP | 1589140 A1 | 10/2005 | |
| EP | 1591574 A1 | 11/2005 | |
| JP | 7-37703 B2 | 4/1995 | |
| JP | 09-188951 A | 7/1997 | |
| JP | 2001-095845 A | 4/2001 | |
| JP | 2003-025471 A | 1/2003 | |
| JP | 2004-244790 A | 9/2004 | |
| JP | 2004-244791 A | 9/2004 | |
| JP | 2006-089907 A | 4/2006 | |
| JP | 2008-030468 A | 2/2008 | |

OTHER PUBLICATIONS

European Search Report for EP 07832511.5, issued Mar. 17, 2011.
Office Action issued to AU Application No. 2007326554, mailed Jul. 8, 2011.

* cited by examiner direction M

COMPOSITE SHEET AND ABSORBENT ARTICLE COMPRISING COMPOSITE SHEET

RELATED APPLICATIONS

The present application is based on International Application Number PCT/JP2007/072786 filed Nov. 26, 2007, and claims priority from Japanese Application Number 2006-319596, filed Nov. 28, 2006, the disclosures of which are hereby incorporated by reference herein in their entirety.

TECHNICAL FIELD

The present invention relates to a composite sheet and an absorbent article using the composite sheet.

BACKGROUND ART

Composite sheets having a plurality of nonwoven fabrics laminated with an adhesive have been conventionally used in various applications and have been subjected to various types of processing in accordance with the intended uses or purposes. When used in an absorbent article, for example, the composite sheet is formed to improve an appearance and texture of the absorbent article, and to stretch along with body movement and the like.

However, in a case where a composite sheet is used in an absorbent article, the composite sheet is required to stretch along with body movement and the like during putting on or during use, without producing discomfort to a wearer. At the same time, the composite sheet is required to have a strength such that the composite sheet does not break in an extended state is required, while maintaining stretchability.

Japanese Unexamined Patent Application First Publication No. Hei 9-188951 discloses a nonwoven fabric that is obtained by jetting a gas toward and pulverizing a thermoplastic polyurethane elastic body, laminating the pulverized body into a sheet-like shape, and fusion-bonding contact points. However, since the nonwoven fabric thus obtained has a high strength, a material to be coupled therewith to obtain a composite sheet is required to have a high basis weight, thus leading to high cost. In addition, in a case where the nonwoven fabric is used for disposable shorts, a tensile strength thereof is higher than an appropriate tensile strength of disposable shorts. Furthermore, polyurethane elastomer generally has a unique sticky texture and is not preferable to be used in an absorbent article.

In addition, Japanese Unexamined Patent Application First Publication No. 2006-89907 discloses a method for developing extensibility while reducing damage to a sheet by performing stretch processing two times on an elastomer and an extensible fiber composite nonwoven fabric. This method causes fiber breakage and structure breakdown of the sheet in the stretch processing, thus greatly decreasing the strength of the composite sheet.

To obtain a necessary strength, it is required that the composite sheet is made to have a high basis weight or made with an extensible fiber having high fracture elongation, thus leading to high cost. Furthermore, higher basis weight, density and the like may degrade the texture of the sheet. On the other hand, in a case where a nonwoven fabric having a low basis weight is used, a sheet may be broken in a manufacturing process or during use of an absorbent article and the like.

DISCLOSURE OF THE INVENTION

Problems to be Solved by the Invention

An objective of the present invention is to provide a composite sheet of a low basis weight having superior texture that can inhibit breakage in a manufacturing process or during use of an absorbent article.

Means for Solving the Problems

The present inventors have discovered that a composite sheet of superior texture that has a low basis weight and can inhibit breakage in a manufacturing process or during use of an absorbent article can be obtained by bonding a stretchable nonwoven fabric formed by mixing an elastomer fiber and a stretchable thermoplastic fiber, in an extended state, to a nonstretchable nonwoven fabric by way of a hot melt adhesive, thereby completing the present invention.

In a first aspect of the present invention, a composite sheet includes: a nonstretchable sheet; a stretchable nonwoven fabric including a thermoplastic fiber that is at least partially stretched and an elastomer fiber that is different from the thermoplastic fiber, in which a plurality of belt-like nondense regions and a plurality of dense regions are formed on both faces along a first direction and alternately arranged to be continuous in a second direction that is orthogonal to the first direction, and the belt-like dense regions on a first face and the belt-like dense regions on a second face are alternately arranged in the second direction; and an adhesive portion that joins the nonstretchable sheet and the stretchable nonwoven fabric, in which a maximum breaking strength in the first direction and the second direction is at least 20 N/50 mm.

According to a second aspect of the present invention, in the composite sheet as described in the first aspect, the thermoplastic fiber includes a partially-unstretched thermoplastic fiber and a partially-stretched thermoplastic fiber that has a smaller average fiber diameter smaller than that of the partially unstretched thermoplastic fiber; a region where the partially-stretched thermoplastic fiber is disposed is the belt-like nondense region; and a region where the partially-unstretched thermoplastic fiber is disposed is the belt-like dense region.

According to a third aspect of the present invention, the composite sheet as described in the first or the second aspect is obtained by adhering the stretchable nonwoven fabric in an extended state to the nonstretchable sheet.

According to a fourth aspect of the present invention, in the composite sheet as described in any one of the first to the third aspects, a basis weight of the stretchable nonwoven fabric in a nonextended state is 200 to 100 g/m$^2$.

According to a fifth aspect of the present invention, in the composite sheet as described in any one of the first to the fourth aspects, strength of the stretchable nonwoven fabric, in an extended state in the second direction to 75% extension, is no greater than 5 N/50 mm.

According to a sixth aspect of the present invention, in the composite sheet as described in any one of the first to the fifth aspects, a basis weight of the nonstretchable sheet in a taught state is 10 to 50 g/m$^2$.

According to a seventh aspect of the present invention, in the composite sheet as described in any one of the first to the sixth aspects, a basis weight of the composite sheet in a nonextended state is no greater than 200 g/m², and a basis weight of the composite sheet in an extended state is no greater than 130 g/m².

According to an eighth aspect of the present invention, in the composite sheet as described in any one of the first to the seventh aspects, a tensile strength of the composite sheet, in an extended state to 60% extension, is no greater than 7 N/50 mm.

In a ninth aspect of the present invention, an absorbent article at least includes: an absorbent core; and the composite sheet as described in any one of the first to the eighth aspects.

In a tenth aspect of the present invention, an absorbent article, which has a longitudinal direction and a width direction that is perpendicular to the longitudinal direction, includes: an absorbent core having a substantially elongated shape, which is disposed along the longitudinal direction; a nonstretchable sheet having a U-shaped cutout portion that is formed on both ends in the width direction to project inward; a first stretchable nonwoven fabric that is disposed on at least any one of a skin contacting side and a skin noncontacting side during use, in a front body that is positioned on a front side of a wearer's body and in a back body that is positioned on a back side of a wearer's body; and a second stretchable nonwoven fabric that is disposed on at least any one of a skin contacting side and a skin noncontacting side, in a region including the most projecting area of the cutout portion in the nonstretchable sheet, in which the first stretchable nonwoven fabric is provided with an adhesive portion that adheres to the nonstretchable sheet and formed to be stretchable in the width direction, the second stretchable nonwoven fabric is provided with an adhesive portion that adheres to the nonstretchable sheet and formed to be stretchable in the longitudinal direction, and a maximum breaking strength, in the longitudinal direction and in the width direction, of a portion where the first stretchable nonwoven fabric and the nonstretchable sheet are joined with each other and of a portion where the second stretchable nonwoven fabric and the nonstretchable sheet are joined with each other is at least 20 N/50 mm.

Effects of the Invention

The present invention can provide a composite sheet of superior texture, which can inhibit breakage in a manufacturing process or during use of an absorbent article, by bonding a stretchable nonwoven fabric formed by mixing an elastomer fiber and a stretchable thermoplastic fiber, in an extended state, to a nonstretchable nonwoven fabric.

PREFERRED MODE FOR CARRYING OUT THE INVENTION

Embodiments of the present invention are described hereinafter. The present invention relates to a composite sheet obtained by subjecting a nonwoven fabric formed by mixing an elastomer fiber and a stretchable thermoplastic fiber to stretch processing to form a stretchable nonwoven fabric, and bonding the stretchable nonwoven fabric in an extended state to a nonstretchable nonwoven fabric with an adhesive. The composite sheet according to the present invention, a manufacturing method of the composite sheet, and an absorbent article using the composite sheet are described in detail hereinafter.

Composite Sheet

Figure 1:
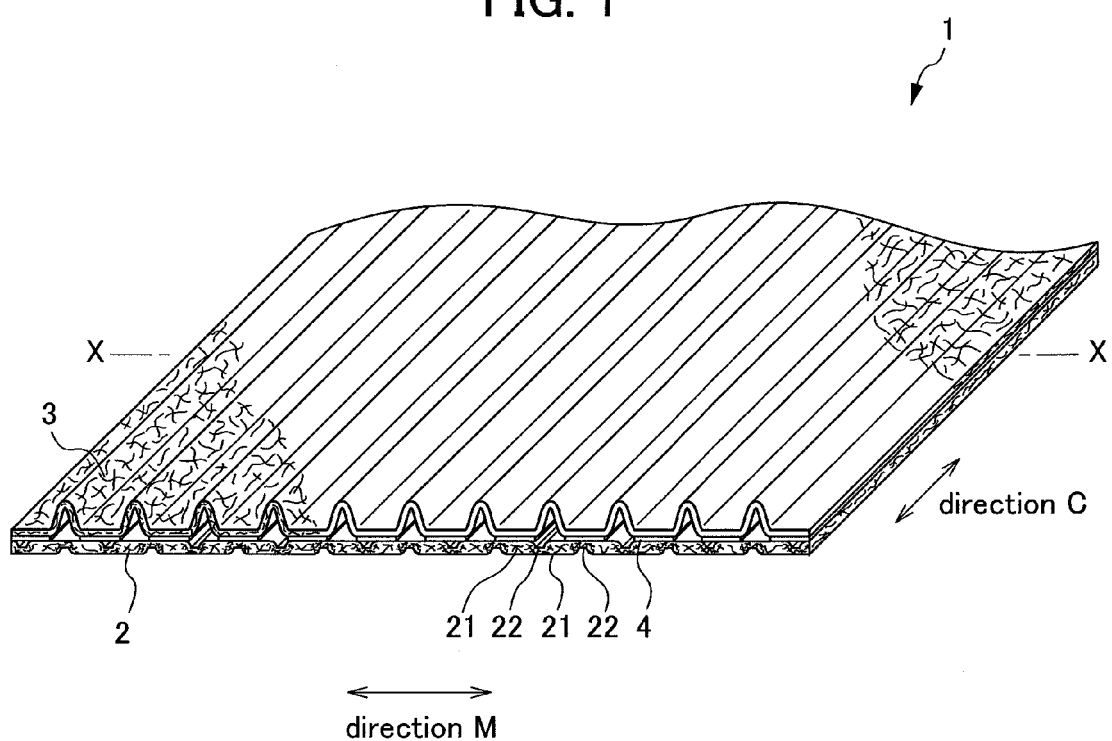
FIG. 1 is a perspective view of a composite sheet according to the present invention.
Figure 2:
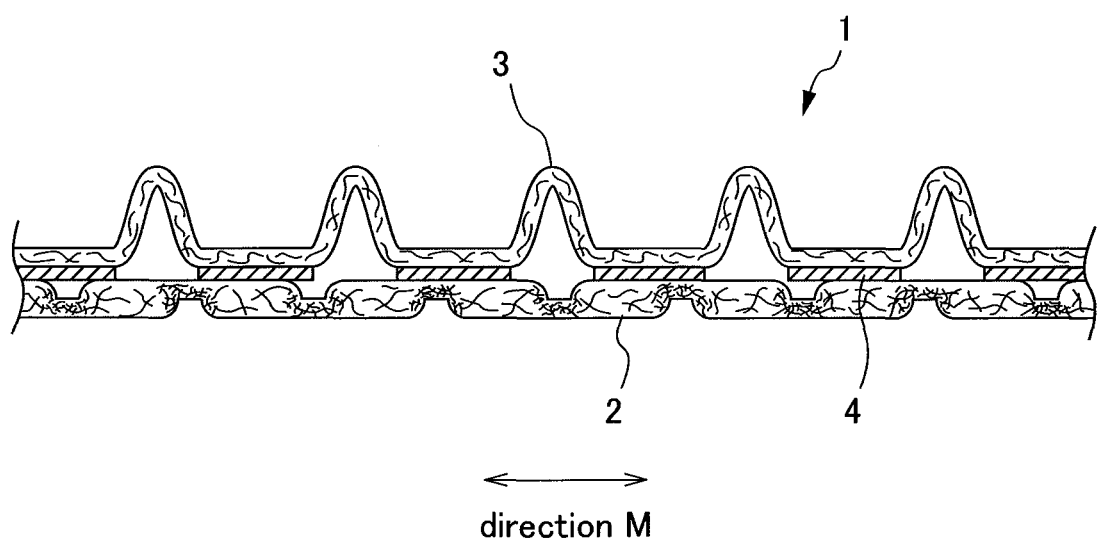
FIG. 2 is an enlarged cross-sectional view along a direction X-X in FIG. 1.

A composite sheet 1 is described with reference to FIGS. 1 to 9. As shown in FIGS. 1 and 2, the composite sheet 1 according to the present invention has a stretchable nonwoven fabric 2 and a nonstretchable nonwoven fabric 3, serving as a nonstretchable sheet, bonded to each other with an adhesive 4. More specifically, in the composite sheet 1, the stretchable nonwoven fabric 2 in an extended state is bonded to the nonstretchable nonwoven fabric 3.

Figure 6A:
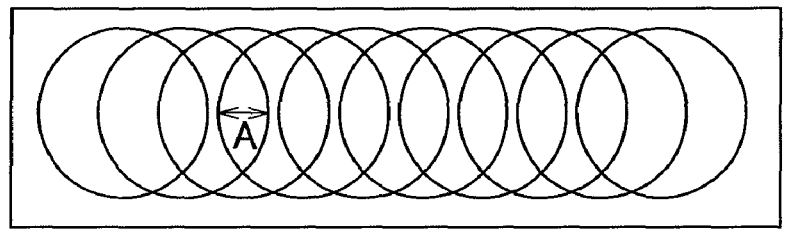
FIG. 6A is a diagram showing an example of a coating pattern of an adhesive according to the present invention.
Figure 6B:
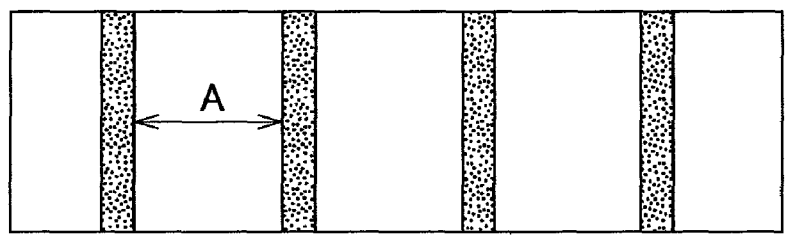
FIG. 6B is a diagram showing an example of a coating pattern of an adhesive according to the present invention.

The composite sheet 1 is formed by applying the adhesive 4 to the nonstretchable nonwoven fabric 3 in strips at predetermined intervals and layering to bond the nonstretchable nonwoven fabric 3 to the stretchable nonwoven fabric 2 in an extended state. Therefore, when the extended state of the stretchable nonwoven fabric 2 is released, the nonstretchable nonwoven fabric 3 is bonded to the stretchable nonwoven fabric 2 in accordance with a coating pattern of the adhesive 4 and has a plurality of wrinkles formed therein, as unbonded portions thereof sag. The form of the wrinkles is not limited to the form shown in FIG. 2 and can be changed depending on the coating pattern of the adhesive 4 (described later). FIG. 2 shows an aspect where the adhesive 4 is applied at equal widths and at regular intervals, as shown in FIG. 6B. The wrinkles in the nonstretchable nonwoven fabric 3 are also formed at substantially regular intervals. Furthermore, the adhesive 4 may be applied to not only the nonstretchable nonwoven fabric 3, but also to the stretchable nonwoven fabric 2.

A basis weight of the composite sheet 1 is preferably no greater than 200 g/m² in a relaxed state. In addition, a basis weight of the composite sheet 1, in a state of being extended to a natural length of the nonstretchable nonwoven fabric 3, is preferably no greater than 130 g/m².

The basis weight of the composite sheet 1 in a state of being extended to a natural length thereof (laminated basis weight) can be obtained by the following equation.

(basis weight of stretchable nonwoven fabric)/(width reduction ratio of stretchable nonwoven fabric)/(stretch ratio of stretchable nonwoven fabric)+(basis weight of nonstretchable nonwoven fabric)

The width reduction ratio of the stretchable nonwoven fabric indicates the ratio of the length in the first direction (direction C), when being extended, of the stretchable nonwoven fabric 2 to the length in the first direction (direction C), when being relaxed (nonextended state), of the stretchable nonwoven fabric 2. When the stretchable nonwoven fabric is extended, a so-called neck-in phenomenon occurs, whereby the length thereof in the first direction (direction C) is reduced.

In addition, a maximum breaking strength of the composite sheet 1 in a lateral direction and in a longitudinal direction is preferably at least 20 N/50 mm, and more preferably at least 40 N/50 mm. In a case where the maximum breaking strength is less than 20 N/50 mm, the composite sheet 1 may be broken, for example, during use of an absorbent article (described later) and the like. Here, the longitudinal direction of the composite sheet 1 corresponds to a first direction (direction C), and the lateral direction corresponds to a second direction (direction M) that is orthogonal to the first direction.

A measuring method of the maximum breaking strength is described hereinafter. First, a strip of 50 mm in width was obtained from the composite sheet 1 in a relaxed state. Then, a maximum strength of the strip before being broken was measured by way of an autograph tensile tester (Autograph Tensile Tester (AG-1KNI) manufactured by SHIMADZU CORPORATION).

In addition, in a case where the composite sheet 1 is used for an absorbent article (described later), the tensile strength thereof in an extended state to 60% extension is preferably no greater than 7 N/50 mm, and more preferably no greater than 6 N/50 mm. In a case where the tensile strength is greater than 7 N/50 mm, an absorbent article using the composite sheet 1 may give a tight sensation to a wearer during use.

The tensile strength of the stretchable nonwoven fabric 2 extended to 60% extension is measured by the following procedure. First, a sample of 150 mm in a stretch direction and 50 mm in a nonstretch direction was obtained from the composite sheet in a relaxed state. Then, a tensile strength thereof was measured by way of an autograph tensile tester (Autograph Tensile Tester (AG-1KNI) manufactured by SHIMADZU CORPORATION). Both ends in the stretch direction of the test piece were held by the machine with a grip spacing (the length of the test piece except for the portion held by the machine) of 100 mm; the test piece was pulled at a speed of 500 mm/min until the test piece had extended to 60% extension (grip spacing of 160 mm); and the tensile strength was measured.

Figure 3:
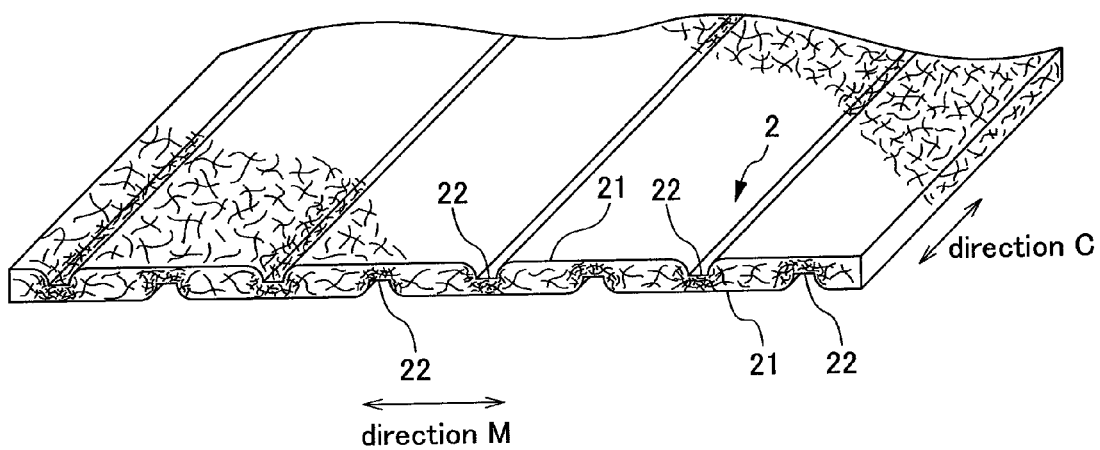
FIG. 3 is a perspective view of a stretchable nonwoven fabric according to the present invention.
Figure 4:
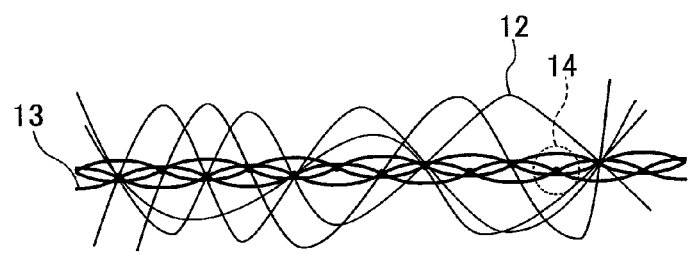
FIG. 4 is a cross-sectional view showing a fiber state of the stretchable nonwoven fabric according to the present invention.

As shown in FIG. 4, the stretchable nonwoven fabric 2 is formed of an elastomer fiber 13 and a stretchable thermoplastic fiber 12. In addition, as shown in FIG. 3, the stretchable nonwoven fabric 2 has a plurality of strip-shaped nondense regions 21 and a plurality of strip-shaped dense regions 22 alternately formed on both surfaces thereof. The plurality of dense regions 22 on a first surface are alternated with the plurality of dense regions 22 on a second surface, in the second direction (direction M) of the composite sheet 1.

The nondense region 21 includes more of the stretchable thermoplastic fiber 12, which has been stretched by gear-stretch processing (described later), than the dense region 22. Furthermore, the dense region 22 includes more of the stretchable thermoplastic fiber 12, which has not been stretched by gear-stretch processing (described later), than the nondense region. That is, in the stretchable nonwoven fabric including the dense region 22 and the nondense region 21 formed by gear-stretch processing, the mass per unit volume of the dense region 22 is higher than the mass per unit volume of the nondense region 21.

In the nondense region 21, although the elastomer fiber 13 contracts to the original fiber length even after gear-stretch processing, the stretchable thermoplastic fiber 12, which has been stretched by gear-stretch processing, is maintained in a partially-extended state without contracting to the original fiber length. The thermoplastic fiber 12 becomes extended in the thickness direction around a compression point 14 by a length corresponding to its extended portion. That is, a gap in the stretchable nonwoven fabric 2 is greater than that before gear-stretch processing. Furthermore, the length of the extended portion of the stretchable thermoplastic fiber 12, which has been at least partially stretched by gear-stretch processing, is an extension margin of the stretchable nonwoven fabric 2 (composite sheet 1).

An example of the stretchable thermoplastic fiber 12, which is used for the stretchable nonwoven fabric 2, includes polyolefin-based and polyester-based fibers. More specifically, polypropylene, polyethylene, polyethylene terephthalate, and polybutylene terephthalate can be used.

Furthermore, an example of the elastomer fiber 13 used for the stretchable nonwoven fabric 2 includes urethane-based, polystyrene-based, and rubber-based fibers. More specifically, polyurethane and the like can be used.

An example of the mixture ratio (ratio by weight) of the elastomer fiber 13 to the stretchable thermoplastic fiber 12 is 80:20 to 25:75. The stretchable nonwoven fabric 2 may be deformed more greatly when the mixture ratio of the stretchable thermoplastic fiber 12 is greater than 75%, and the stretchable nonwoven fabric 2 may give a sticky sensation when the mixture ratio of the elastomer fiber 13 is greater than 80%.

To obtain a necessary strength for the composite sheet 1, the basis weight of the stretchable nonwoven fabric 2 in a relaxed state is preferably 20 to 100 g/m$^2$. With a basis weight less than 20 g/m$^2$, an amount of the adhesive 4 flowing out may be greater. On the other hand, with the basis weight greater than 100 g/m$^2$, even if the nonwoven fabric 2 is subjected to gear-stretch processing in the transverse direction (direction M), the strength of the stretchable nonwoven fabric 2 in an extended state to 75% extension may exceed 10 N/50 mm, and thus the absorbent article using the composite sheet 1 may give a wearer a tight sensation. The tensile strength in a case of 75% extension can be measured by the abovementioned procedure for measuring the tensile strength in a case of 60% extension.

In the stretchable nonwoven fabric 2, a basis weight of the stretchable thermoplastic fiber 12 in a relaxed state is preferably 4 to 60 g/m$^2$. With a basis weight less than 4 g/m$^2$, it is difficult to obtain a superior texture. On the other hand, with a basis weight greater than 60 g/m$^2$, the composite sheet becomes too rigid. In addition, in the stretchable nonwoven fabric 2, a basis weight of the elastomer fiber 13 is preferably 5 to 70 g/m$^2$. With a basis weight less than 5 g/m$^2$, it is difficult to obtain a composite sheet having sufficient stretchability. Alternatively, with a basis weight greater than 70 g/m$^2$, the tensile strength becomes too high and it is difficult to obtain a usable composite sheet.

In addition, in a case where the stretchable nonwoven fabric 2 is formed under the abovementioned conditions, strain magnitude is preferably no greater than 10%. With a strain magnitude greater than 10%, the shrinkage size of a final product becomes unstable, and thus absorbent articles made with the composite sheet 1 may give inconsistent sensations during use.

The stretchable nonwoven fabric 2 includes a stretchable thermoplastic fiber 12 and an elastomer fiber 13, and is formed by subjecting a raw stretchable nonwoven fabric 5 that is not in an extended state to gear-stretch processing. The raw stretchable nonwoven fabric 5 is formed of the abovementioned fiber structure.

Gear-stretch processing indicates processing for compressing the raw stretchable nonwoven fabric 5 by a pair of shaping rollers 10 and 10', extending the stretchable thermoplastic fiber 12, and causing the raw stretchable nonwoven fabric 5 to have stretchability based on the stretchability of the elastomer fiber 13. Gear-stretch processing is described with reference to FIG. 5.

Each of the paired shaping rollers 10 and 10' used for gear-stretch processing includes a toothed region 11 having a plurality of grooves or a plurality of gear teeth 111. The shaping rollers 10 and 10' rotate opposite to each other with their toothed regions 11 meshed with each other in order to compress the raw stretchable nonwoven fabric 5. A dense region 22 is formed in a portion that is compressed by an apex portion of the meshed gear tooth 111 in the raw stretchable nonwoven fabric 5. Furthermore, a portion that is not compressed by the gear tooth 111 in the raw stretchable nonwoven fabric 5 (a portion in contact with a side surface of the gear tooth 111) is extended by the meshed gear tooth 111 so that the fiber extends, thereby forming the nondense region 21.

The plurality of nondense regions 21 and the plurality of dense regions 22 are thus alternately formed in a strip shape for each gap between the teeth 111 in the toothed region 11. In other words, the nondense regions 21 and the dense regions 22 are alternately formed parallel to the longitudinal direction (direction C) in the stretchable nonwoven fabric 2.

As described above, the plurality of nondense regions 21 and the plurality of dense regions 22 are alternately formed with substantially equal spacing in accordance with the shape at the tip of each of the gear teeth 111 and the depth of the groove formed by the two adjacent gear teeth 111. In other words, the length in the longitudinal direction (direction C) of the nondense region 21 and the dense region 22 is determined in accordance with the size of the gear teeth 111 in the pair of shaping rollers 10 and 10'.

Shapes that can be used for the shape at the tip of the gear tooth 111 are an acute-angled shape, a shape having a substantially flat surface at its top, or a shape that is substantially circular in a cross section parallel to a concentric shape of the shaping rollers 10 and 10'.

Furthermore, the stretch direction of the stretchable nonwoven fabric 2 can be optionally formed in accordance with the intended use of the stretchable nonwoven fabric 2 or the composite sheet 1. That is, the stretchable nonwoven fabric 2 can be extended in one of the transverse direction (direction M) and the longitudinal direction (direction C) depending on the direction in which the toothed regions 11 are arranged when gear-stretch processing is performed. For example, when the toothed region 11 is arranged so as to be perpendicular to the transverse direction (direction M) of the raw stretchable nonwoven fabric 5 before gear-stretch processing, the stretchable nonwoven fabric 2 extends in the transverse direction (direction M). Alternatively, when the toothed region 11 is arranged so as to be parallel to the transverse direction (direction M) of the raw stretchable nonwoven fabric 5 before gear-stretch processing, the stretchable nonwoven fabric 2 extends in the longitudinal direction (direction C). Furthermore, gear-stretch processing is performed twice in the transverse direction (direction M) and the longitudinal direction (direction C) so that a stretchable nonwoven fabric 2 can be formed that can be stretched in both of the directions.

In order to inhibit the adhesive 4 from flowing out, it is preferable for the respective average fiber diameters of the stretchable thermoplastic fiber 12 and the elastomer fiber 13, which constitute the stretchable nonwoven fabric 2, to be made to be as small as possible. This can inhibit generation of a large gap, even with the same basis weight and the same density. Flowing out of the adhesive 4 (described later) can also be inhibited. More specifically, an average fiber diameter of the stretchable thermoplastic fiber 12 and the elastomer fiber 13, which are used for the stretchable nonwoven fabric 2, is preferably 10 to 35 μm.

It can be expected that the average fiber diameter of the stretchable thermoplastic fiber 12 in the nondense region 21 is smaller than the average fiber diameter of the stretchable thermoplastic fiber 12 in the dense region 22, due to extension by the gear-stretch processing.

Examples of the nonstretchable nonwoven fabric 3 to be laminated on the abovementioned stretchable nonwoven fabric 2 include various types of known nonwoven fabrics such as a spunbonded nonwoven fabric, a meltblown nonwoven fabric, an SMS nonwoven fabric that is a combination of a spunbonded nonwoven fabric and a meltblown nonwoven fabric, an air-through nonwoven fabric, a spun-lace nonwoven fabric, and an airlaid nonwoven fabric, which can be changed, as needed, in accordance with the intended use. Furthermore, the nonstretchable nonwoven fabric 3 to be bonded is not limited to a single layer, and may be multi-layer. Alternatively, it may be partially multi-layer in accordance with the intended use.

A basis weight of the nonstretchable nonwoven fabric 3 is preferably 10 to 50 g/m$^2$ in an extended state. In a case where the basis weight of the nonstretchable nonwoven fabric 3 is less than 10 g/m$^2$, the maximum strength of the composite sheet 1 may be insufficient. On the other hand, in a case where the basis weight of the nonstretchable nonwoven fabric 3 is greater than 50 g/m$^2$, the return strength of the nonstretchable nonwoven fabric 3 is insufficient with respect to the rigidity thereof, and thus there may be a case where a degree of elongation of the composite sheet 1 may not be obtained.

The composite sheet 1 is formed by bonding the stretchable nonwoven fabric 2 and the nonstretchable nonwoven fabric 3 to each other with the adhesive 4. The adhesive 4 to be used is preferably a hot-melt adhesive. The composite sheet 1 is formed by bonding the stretchable nonwoven fabric 2 in an extended state to the nonstretchable nonwoven fabric 3 with the adhesive 4.

At this time, it is preferable that the stretchable nonwoven fabric 2 is bonded to the nonstretchable nonwoven fabric 3, the stretchable nonwoven fabric 2 being extended such that the length thereof is increased by a predetermined factor. In this way, with the extension released after the stretchable nonwoven fabric 2 and the nonstretchable nonwoven fabric 3 are bonded to each other, wrinkles are formed in the nonstretchable nonwoven fabric 3 as the stretchable nonwoven fabric 2 contracts. As shown in FIG. 2, the nonstretchable nonwoven fabric 3 is partially bonded and fixed to the stretchable nonwoven fabric 2 with the adhesive 4, so that the entire composite sheet 1 stretches due to the wrinkles formed in the nonstretchable nonwoven fabric 3 used as an extension margin.

The adhesive 4 may be applied to either the stretchable nonwoven fabric 2 or the nonstretchable nonwoven fabric 3. Furthermore, as a method/pattern for applying the hot-melt adhesive, any method/pattern can be selected from pattern processing such as curtain spray, spiral, omega, dot shape, full coating, dot aggregate, slot coating, and roller coating.

When a pattern other than curtain spray or the full coating is selected, it is preferable that spacing A between adjacent hot-melt joints (see FIGS. 6A and 6B) is less than 15 mm, and more preferably less than 10 mm. For example, the coating pattern of the adhesive 4 shown in FIG. 6A is the spiral pattern, and the coating pattern shown in FIG. 6B is an intermittent coating pattern by the roller coating. When the spacing A between the joints becomes enlarged, the appearance is degraded because the appearance of wrinkles is increased, and fingers enter a nonjoining portion when the nonwoven fabric is used for an absorbent article, described later, thereby causing a break to occur.

Figure 7:
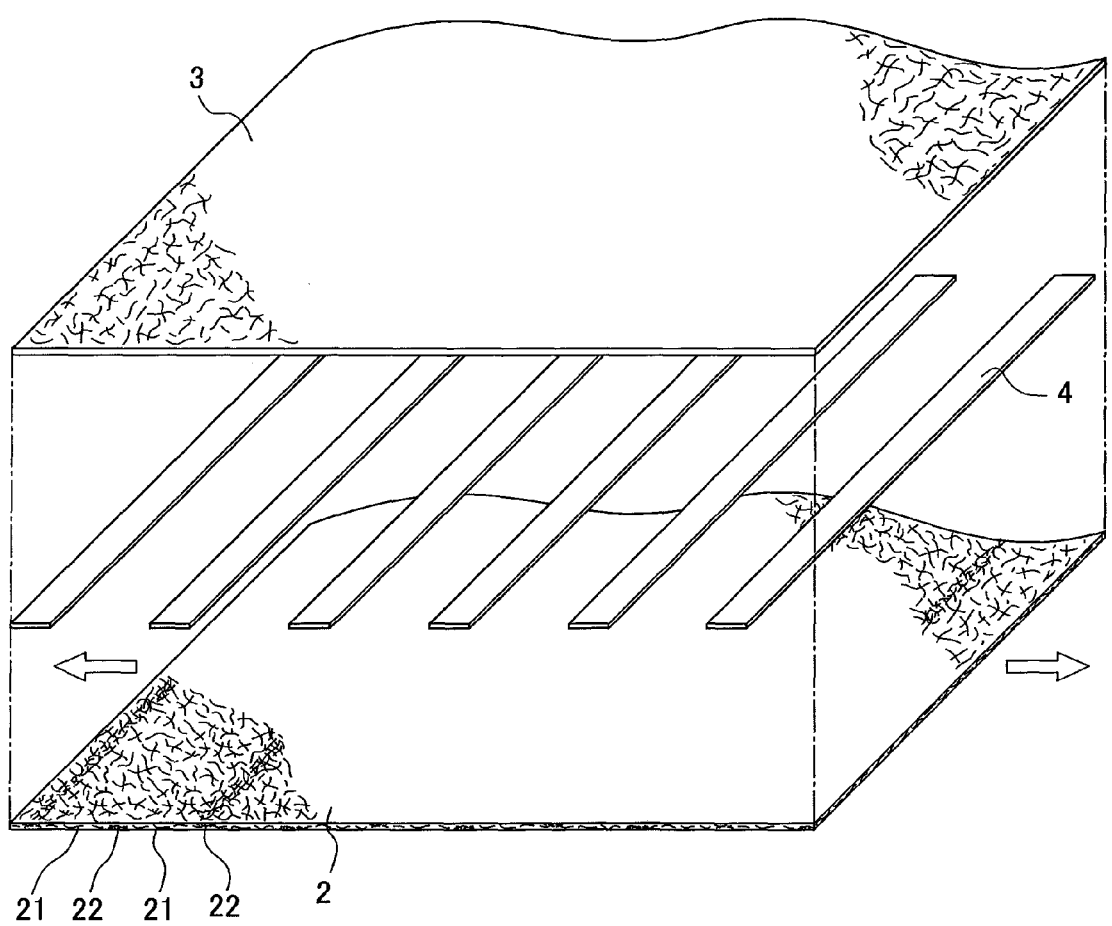
FIG. 7 is a diagram showing an example in which the stretchable nonwoven fabric according to the present invention is coated with an adhesive in the coating pattern shown in FIG. 6B.
Figure 8:
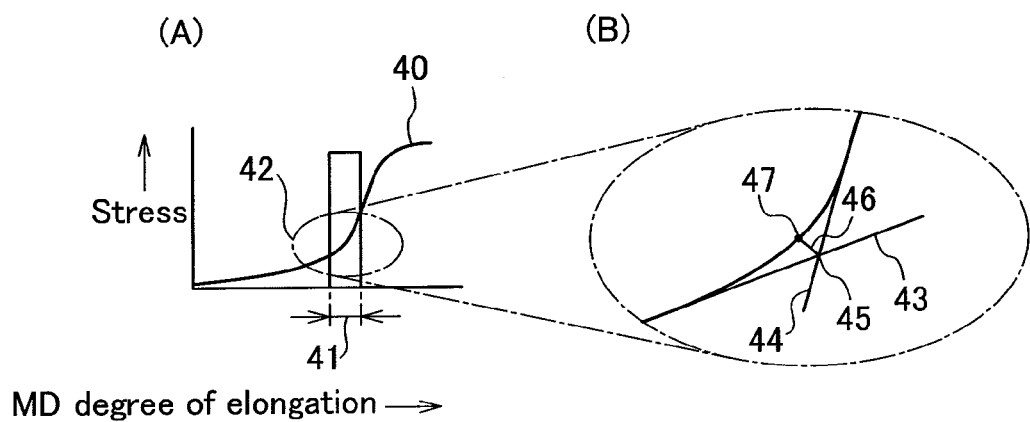
FIG. 8A is a diagram illustrating tensile strength per predetermined width of the composite sheet according to the present invention in an extended state.
FIG. 8B is a partial enlarged view of FIG. 8A.

The adhesive 4 is applied to the stretchable nonwoven fabric 2 in a strip shape with equal spacing, and is bonded to the nonstretchable nonwoven fabric 3, as shown in FIG. 7, for example.

In addition, a basis weight of the adhesive 4 is preferably 0.5 to 15 g/m$^2$. In a case where the basis weight is smaller than 0.5 g/m$^2$, the nonwoven fabrics may, in some cases, be separated. Alternatively, in a case where the basis weight is greater than 15 g/m$^2$, the flexibility of the composite sheet is degraded, and thus the adhesive 4 may flow out.

The flowing of the adhesive 4 in the composite sheet 1 according to the present invention can be measured by the average peel strength. When the average peel strength is high, the adhesive 4 flows out so that the stretchable nonwoven fabric is bonded to others. Consequently, the lower the peel strength is, the less the flowing of the adhesive is.

The average peel strength is measured in the following way. A raw stretchable nonwoven fabric 5 is subjected to gear-stretch processing to form a stretchable nonwoven fabric 2. Thereafter, the stretchable nonwoven fabric 2 thus formed is extended to 180%, and is bonded with a nonstretchable nonwoven fabric 3 to obtain a composite sheet 1. Furthermore, the composite sheet 1 is passed between nip rollers at a linear pressure of 3.0 kg/cm. Two pieces of such a composite sheet 1 are manufactured. The two pieces of the composite sheet 1 are brought into a relaxed state, and are overlapped such that their surfaces on the side of the stretchable nonwoven fabrics 2 face each other after being cut to dimensions of 100 mm in the transverse direction (direction M) and 50 mm in the longitudinal direction (direction C). A mass weighing 40 g/cm$^2$ is placed thereon. An example of the mass weighing 40 g/cm$^2$ is a weight having dimensions of 50 mm by 50 mm and weighing 1 kg. Thereafter, an average peel strength (unit of N/50 mm) of a sample left for one week at a temperature of 50° C. and a humidity of 60% is measured by a width of 50 mm, a grip spacing set to 30 mm and at a peel rate of 100 mm/min using a tensile tester (Autograph Tensile Tester (AG-1kNI) manufactured by SHIMADZU CORPORATION).

The average peel strength is preferably 0 to 0.07 N/50 mm. In a case where it exceeds 0.07 N/50 mm, it is likely that tackiness will be felt when wearing an absorbent article using the composite sheet 1. Furthermore, adjacent pieces may stick together within a package of the absorbent article and a folded product may be difficult to spread.

It is preferable for the stretch ratio of the composite sheet 1 to be no less than 20%. Furthermore, it is preferable for the stretch ratio of the stretchable nonwoven fabric 2 to have a degree of fully-stretched elongation is no less than 20%.

Here, when two tangents 43 and 44 to a curve 40 in a tensile test shown in FIG. 8A are drawn (FIG. 8B), a line 46 for dividing an angle formed by the two tangents into two equal parts is drawn, starting from an intersection 45 thereof, and the intersection of the line 46 and the curve 40 is taken as a point 47. Then, the degree of fully-stretched elongation is at the point 47.

Here, a method for measuring the stretch ratio of the composite sheet 1 is described. First, let Y be the length of the composite sheet 1 with the composite sheet 1 extended to the fully-stretched length in a stretch direction thereof (the original length thereof at the moment where the nonstretchable nonwoven fabric 3 is bonded with the stretchable nonwoven fabric 2), and y be the contraction length of the composite sheet 1 that is obtained after being relaxed from extension and naturally contracted. Y and y are substituted in the following equation.

Stretch Ratio (%)=$Y/y \times 100-100$

The stretch ratio can also be obtained by: putting marks at regular intervals (e.g., 100 mm) in the stretch direction on the composite sheet 1 in a relaxed state; measuring the length between the marks on the composite sheet 1 in a fully extended state in the stretch direction; and applying the foregoing equation.

The stretch ratio can also be obtained by: putting marks at regular intervals (e.g., 100 mm) in the stretch direction on the composite sheet 1 in a relaxed state; measuring the length between the marks on the composite sheet 1 in a state of being extended to a maximum extension in the stretch direction; and applying the foregoing equation.

The respective directions of the stretchable nonwoven fabric 2 and the nonstretchable nonwoven fabric 3 at the time of bonding can be optionally selected in accordance with the intended use or the like of the composite sheet 1. For example, when the stretchable nonwoven fabric 2 has stretch properties in the transverse direction (direction M), the nonstretchable nonwoven fabric 3 can be selected to be either the transverse direction (direction M) or the longitudinal direction (direction C). When the stretchable nonwoven fabric 2 has stretch properties in the longitudinal direction (direction C), the stretchable nonwoven fabric 3 can also be selected to be either the transverse direction (direction M) or the longitudinal direction (direction C). Furthermore, even when the composite sheet 1 is composed of three or more layers, the nonwoven fabric to be bonded can be selected to be both the transverse direction (direction M) and the longitudinal direction (direction C).

A combination of the directions of bonding between the stretchable nonwoven fabric 2 and the nonstretchable nonwoven fabric 3 can be optionally selected in accordance with the intended use or the like. Therefore, by considering the most suitable balance corresponding to the intended use, the composite sheet 1 can be manufactured for the tensile strength. The reason for this is that the nonwoven fabric generally varies in the maximum strength depending on whether it is selected to be the longitudinal direction (direction C) or the transverse direction (direction M). Furthermore, the stretchable nonwoven fabric 2 also differs in tensile strength even in the same basis weight depending on the direction in which gear-stretch processing is performed.

Manufacturing Method of Composite Sheet

Figure 9:
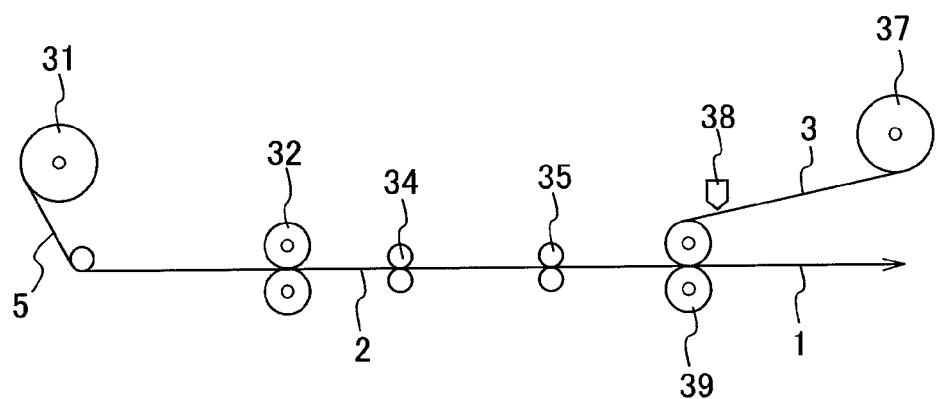
FIG. 9 is a diagram illustrating a manufacturing method of the composite sheet according to the present invention.

A method of manufacturing a composite sheet 1 is described with reference to FIG. 9. The method of manufacturing the composite sheet 1 according to the present invention is carried out in the following way. First, a raw stretchable nonwoven fabric 5 before gear-stretch processing, which is wound around a raw fabric roll 31, is unwound.

Gear-stretch processing is then performed. The raw stretchable nonwoven fabric 5 is inserted between a pair of gear rollers 32 formed such that their respective toothed regions 11 mesh with each other, as described above (FIG. 5). A stretchable thermoplastic fiber 12, which is sandwiched between the teethed regions 11, is extended. As the stretch direction, either the transverse direction (direction M) or the longitudinal direction (direction C) can be selected in accordance with the intended use of the composite sheet 1. The raw stretchable nonwoven fabric 5 can be subjected to gear-stretch processing twice in different directions in a case where the composite sheet 1 is made stretchable in both of the directions. That is, after stretch properties are developed in one of the transverse direction (direction M) and the longitudinal direction (direction C), gear-stretch processing is performed in the other direction for the second time. It should be noted that, in order to make the composite sheet 1 stretchable in both of the directions, gear-stretch processing need not necessarily be performed twice. The composite sheet 1 can be made stretchable in both of the directions by performing gear-stretch processing in the transverse direction (direction M) in the present embodiment.

A stretchable nonwoven fabric 2 having stretchability developed is extended by rollers 34 and 35, and is further passed between nip rollers 39. Alternatively, a nonstretchable nonwoven fabric 3 wound around a raw fabric roll 37 is coated with hot-melt adhesive using an adhesive coater 38, and is passed between the paired nip rollers 39. The stretchable nonwoven fabric 2 and the nonstretchable nonwoven fabric 3 can be laminated by simultaneously passing the stretchable nonwoven fabric 2 and the nonstretchable nonwoven fabric 3 between the nip rollers 39. Thereafter, the composite sheet 1 can be obtained by releasing an extended state.

Absorbent Article

The composite sheet 1 according to the present invention can be employed for an underwear-type disposable diaper 50 serving as an absorbent article, for example. Although an underwear-type disposable diaper 50 using the above-mentioned composite sheet 1 is described in detail below, a surface, directed toward the body of a wearer, of the underwear-type disposable diaper 50 is considered a skin contacting side, and a surface on the opposite side of the skin contacting side is considered a skin noncontacting side.

Figure 10:
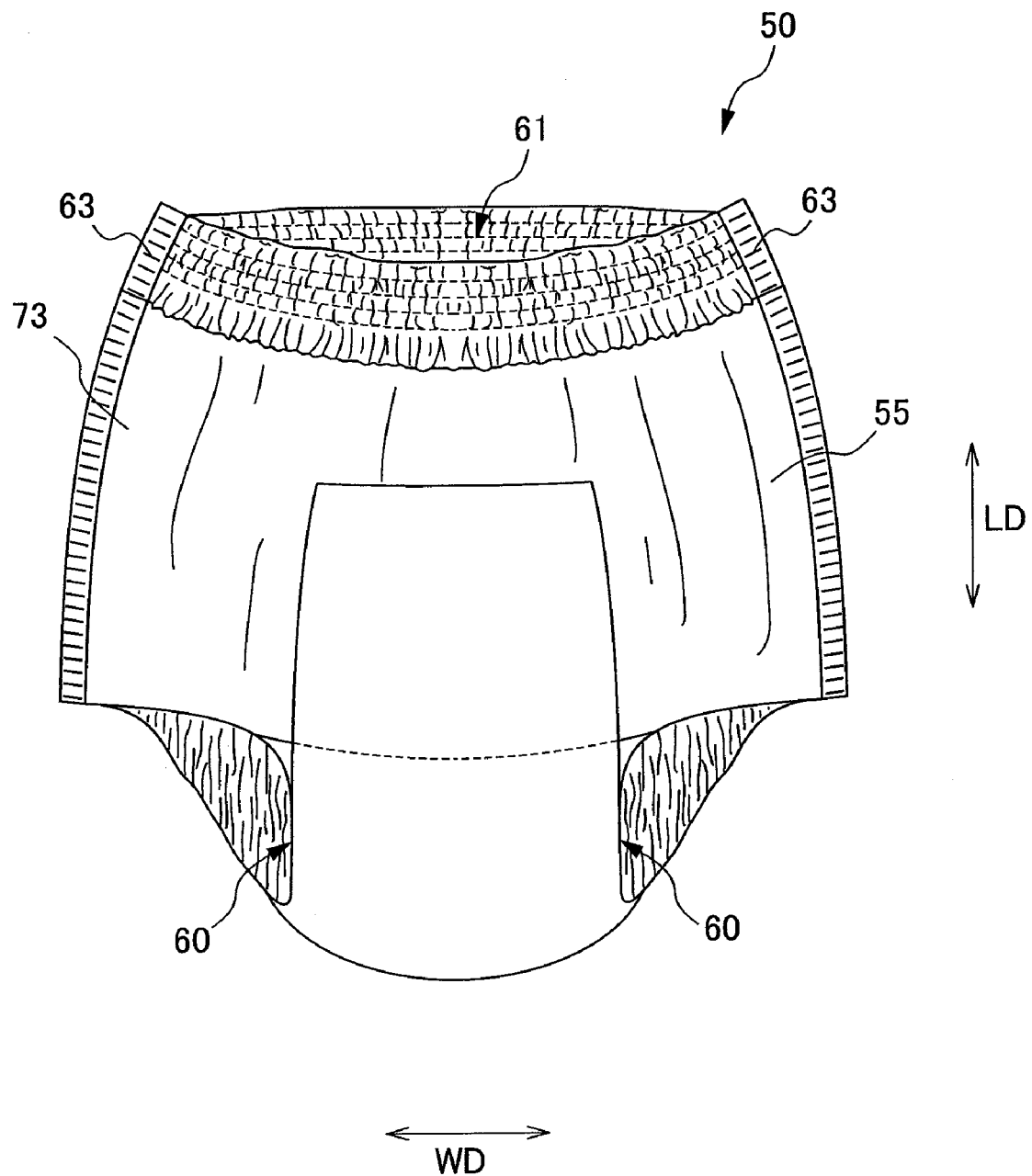
FIG. 10 is a front view showing a disposable diaper as an example of an absorbent article using the composite sheet according to the present invention.
Figure 11:
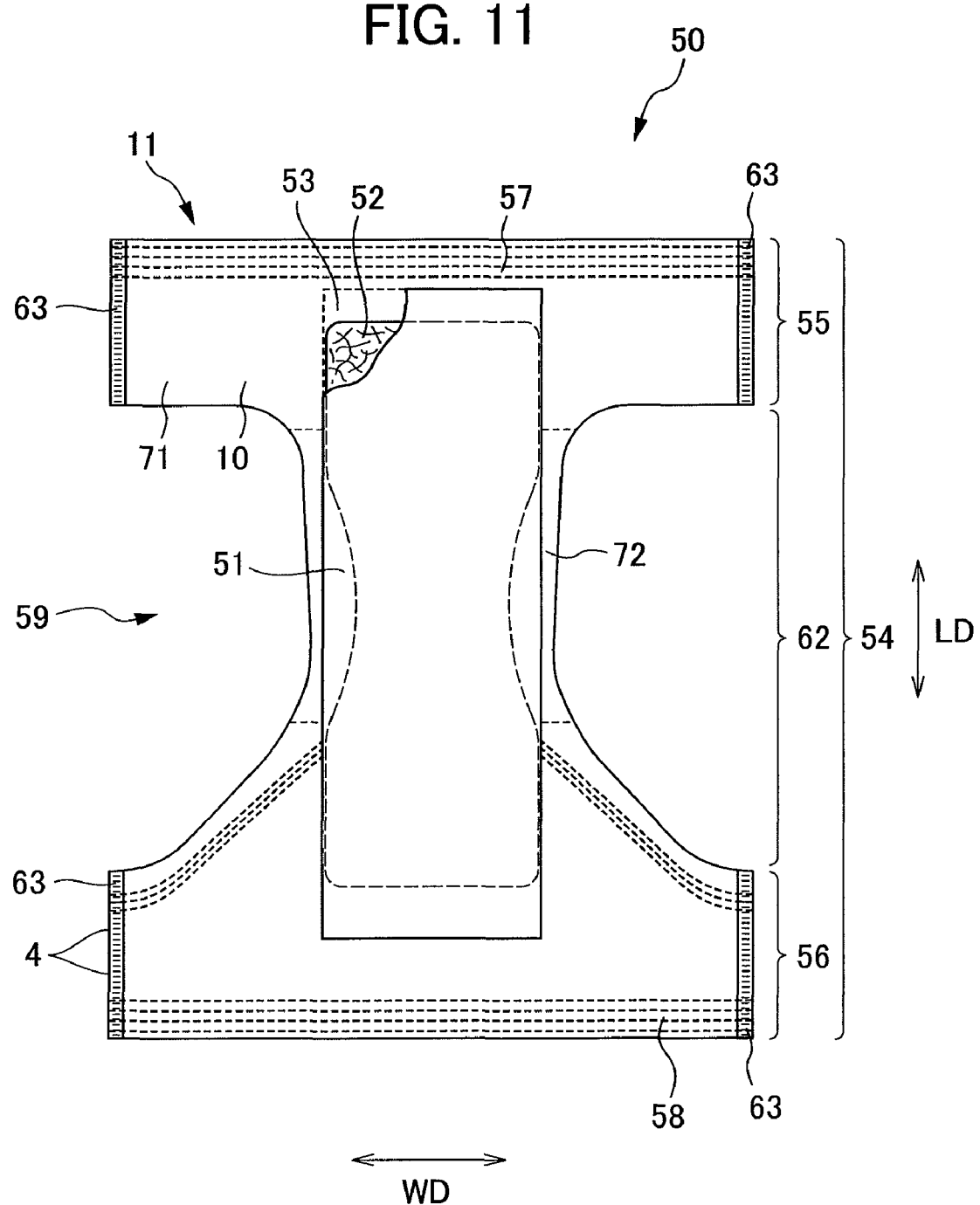
FIG. 11 is a developed view of the disposable diaper according to the present invention.

As shown in FIGS. 10 and 11, an underwear-type disposable diaper body includes a chassis 54 forming the main body of the underwear-type disposable diaper 50, a liquid-permeable front surface sheet 51 arranged on a surface, on the skin contacting side of the chassis 54, a liquid impermeable back surface sheet 53 arranged on a surface on the skin noncontacting side of the chassis 54, and an absorbent core 52 having liquid retaining properties and sandwiched between the front surface sheet 51 and the chassis 54.

Figure 5:
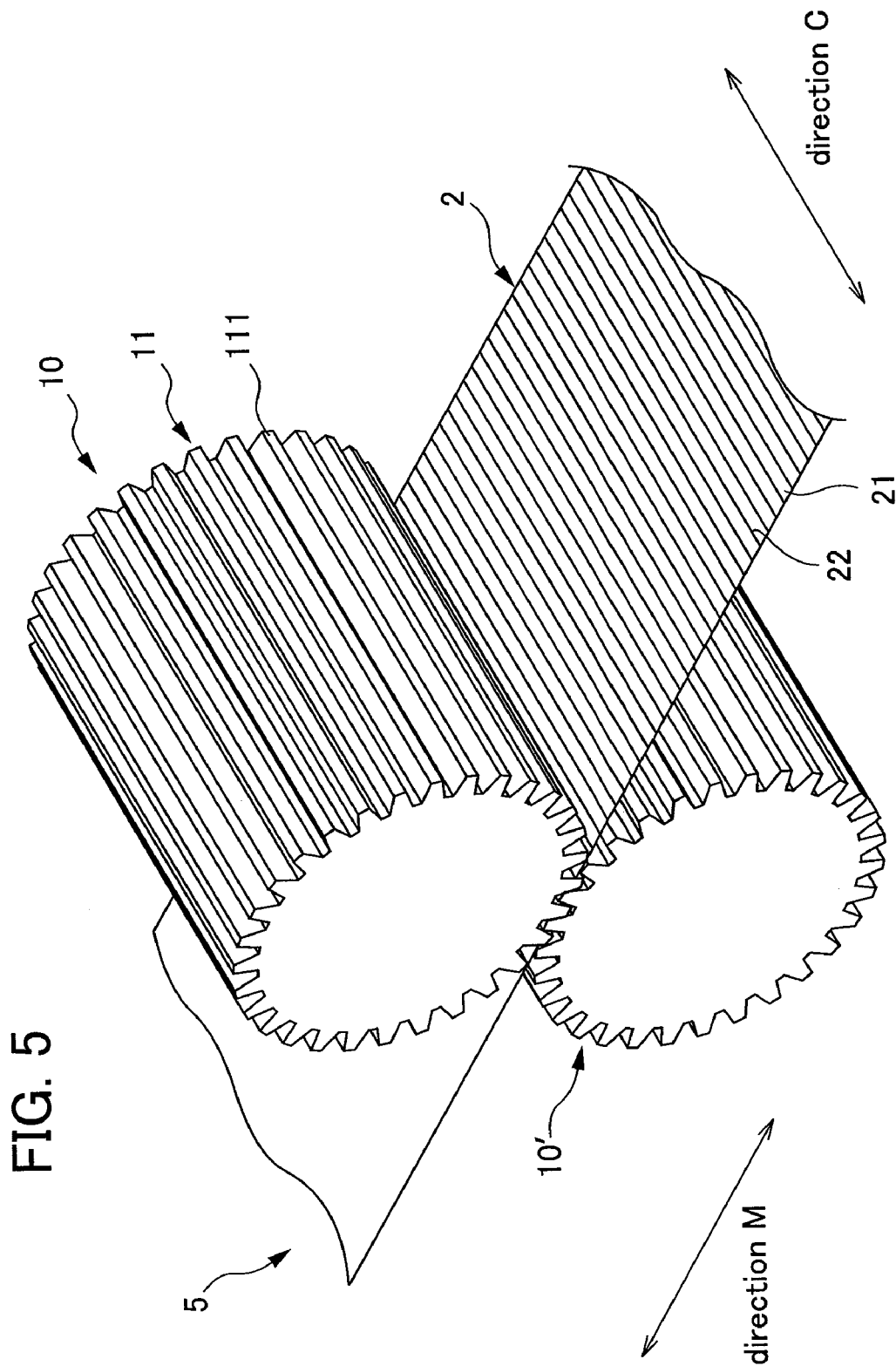
FIG. 5 is a schematic diagram illustrating a formation of the stretchable nonwoven fabric by performing stretch processing on a raw stretchable nonwoven fabric according to the present invention by way of a mesh embossing roller.

The chassis 54 is formed in the shape of underwear by a front body portion 55 and a rear body portion 56, and includes a front waist gather 57 forming an end of the front body portion 55 and a rear waist gather 58 forming an end of the rear body portion 56. The gathers are formed by arranging an elastic member such as a rubber thread around the trunk of the wearer so as to be substantially parallel thereto along a width direction (WD) at respective ends of the front body portion 55 and the rear body portion 56. Here, the width direction (WD) refers to a direction around the trunk of the wearer with the underwear-type disposable diaper 50 worn on the body of the wearer. A direction perpendicular to the width direction (WD) is taken as a longitudinal direction (LD). Therefore, when the stretchable nonwoven fabric 2 that has been subjected to gear-stretch processing in the transverse direction (direction M), as shown in FIG. 5, is used, the front body portion 55 has stretchability in the width direction (WD) when the direction in which the stretchable nonwoven fabric 2 stretches (the direction M) is along the width direction (WD) of the front body portion 55, for example. Cuts 59 having a substantially U-shape are respectively formed toward the inside of the chassis 54 on both sides in the longitudinal direction (LD) of the chassis 54. The cuts 59 respectively form leg openings 60 when the front body portion 55 and the rear body portion 56 of the chassis 54 are joined to each other by joining portions 63 to have the shape of underwear, as shown in FIG. 10. Furthermore, the front body portion 55 and the rear body portion 56 are joined to each other to form a waist opening 61.

As shown in FIG. 11, the chassis 54 includes a crotch region 62. The crotch region 62 is sandwiched between the cuts 59 on both sides thereof. The absorbent core 52 having liquid retaining properties formed in a substantially vertically-long shape composing an absorbing layer is arranged on a surface on the skin contacting side of the crotch region 62. Furthermore, the liquid-permeable front surface sheet 51 and the liquid-impermeable back surface sheet 53 are arranged on a surface on the skin contacting side of the absorbent core 52 and on a surface on the skin noncontacting side of the crotch region 62, respectively.

Here, the chassis 54 includes a base sheet 71 serving as a nonstretchable nonwoven fabric, a pair of crotch-side sheets 72 serving as a first stretchable nonwoven fabric formed of the stretchable nonwoven fabric 2 arranged so as to have stretchability in the longitudinal direction (LD) of the absorbent core 52, and a sheathing sheet 73 serving as a second stretchable nonwoven fabric formed of the stretchable nonwoven fabric 2 arranged so as to have stretchability in the width direction (WD).

The nonstretchable base sheet 71 is a spunbonded nonwoven fabric weighing 19 g/m$^2$, for example, and serves as a main body portion constituting the chassis 54. That is, the crotch-side sheets 72 and the sheathing sheet 73, described later, are joined to a surface on the skin noncontacting side of the base sheet 71 to constitute the chassis 54.

The crotch-side sheets 72 are respectively arranged in both side parts of the crotch region 62 in the chassis 54 and on the surface on the skin noncontacting side, of the base sheet 71. The crotch-side sheet 72 is a nonwoven fabric having stretch properties in the longitudinal direction (LD) and having no stretch properties in the width direction (WD). In other words, the crotch-side sheet is formed by, for example: gear-stretching the stretchable nonwoven fabric 2 in the longitudinal direction (direction C) (which can be performed by placing the gear tooth 111 in FIG. 5 in a machine direction (MD: direction M) so that the stretch direction of the stretchable nonwoven fabric 2 is in a cross direction (CD: direction C); extending the stretchable nonwoven fabric 2 in the longitudinal direction (direction C) to a length 1.9 times greater than the original length thereof; disposing the stretchable nonwoven fabric 2 so that the stretch direction thereof is in the longitudinal direction (LD); and bonding the stretchable nonwoven fabric 2 to the base sheet 71 (the nonstretchable nonwoven fabric 3) with hot-melt adhesive. That is, the crotch-side sheet 72 is a composite sheet 1 joined to the base sheet 71.

The sheathing sheet 73 is a stretchable nonwoven fabric 2 arranged so as to cover the surface on the skin noncontacting side of the base sheet 71 in the chassis 54 and the whole surface other than the front waist gather 57 and the rear waist gather 58. The sheathing sheet 73 is formed to be stretchable in the width direction (WD) and not stretchable in the longitudinal direction (LD). In other words, the sheathing sheet 73 is formed by, for example: gear-stretching the stretchable nonwoven fabric 2 in the lateral direction (direction M) (FIG. 5); extending the stretchable nonwoven fabric 2 to a length 1.8 times greater than the original length thereof; disposing the stretchable nonwoven fabric 2 so that the stretch direction thereof is in the width direction (WD); and bonding the stretchable nonwoven fabric 2 to the base sheet 71 (the non-stretchable nonwoven fabric 3) with hot-melt adhesive. That is, the sheathing sheet 73 is a composite sheet 1 joined to the base sheet 71.

Thus, the chassis 54 is a composite sheet 1, which is partially triple layered, obtained by arranging crotch-side sheets 72 on a surface on the side of the skin noncontacting side of the base sheet 71 and on both sides of the crotch region 62, further arranging the sheathing sheet 73 on the surface on the skin noncontacting side, and respectively joining both the crotch-side sheets 72 and the sheathing sheet 73 to the base sheet 71 with hot-melt adhesive.

When the front body portion 55 and the rear body portion 56 in the chassis 54 are joined to each other to have the shape of underwear, the leg openings (FIG. 10) have stretch properties along the cuts 59 by the crotch-side sheets 72. Furthermore, the front body portion 55 and the rear body portion 56 have stretch properties along the outer periphery of the shape of underwear by the sheathing sheet 73. Therefore, in the underwear-type disposable diaper 50, the chassis 54 itself has stretch properties with movement of the body.

Manufacturing Method of Absorbent Article

Figure 12:
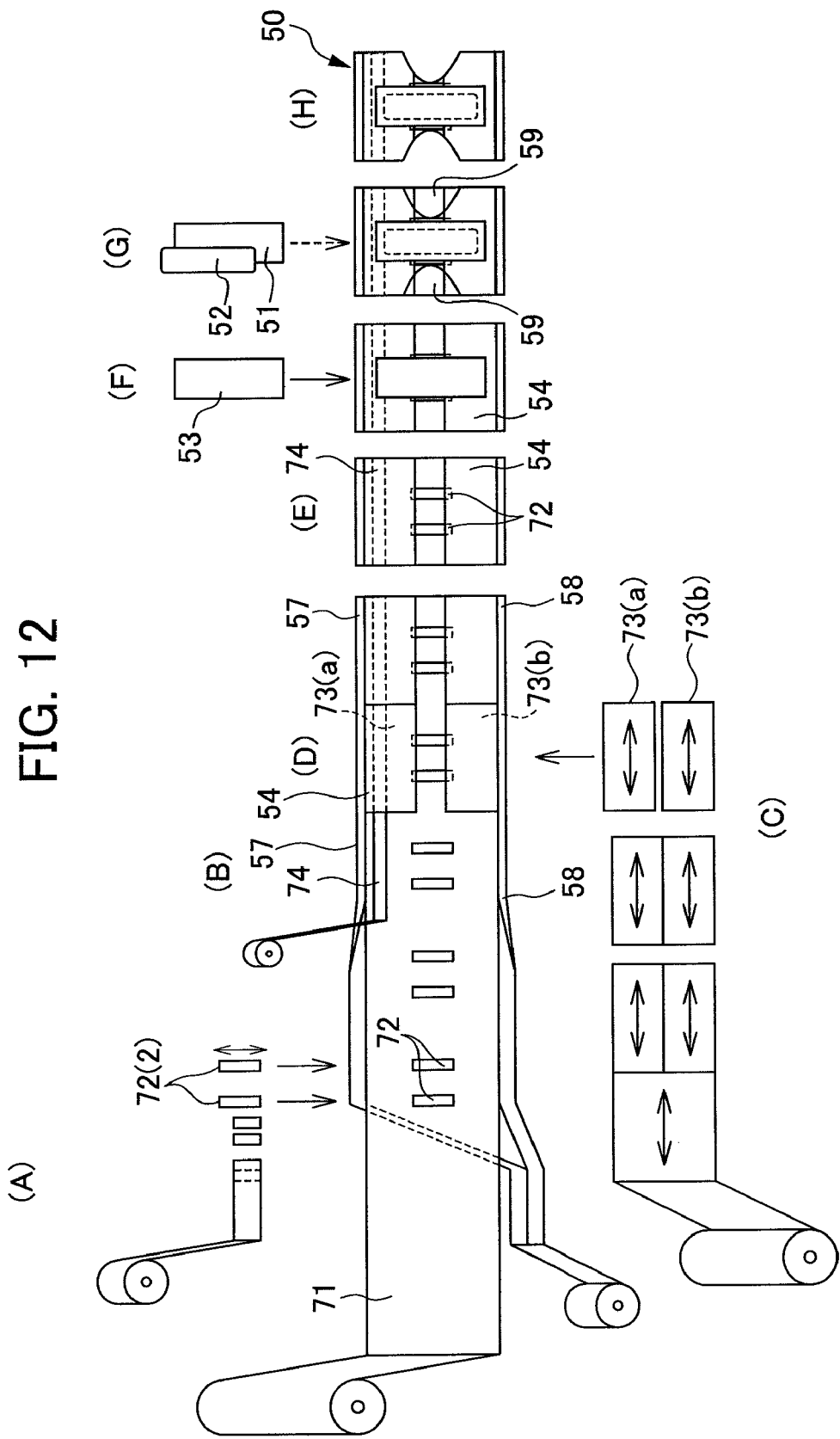
FIG. 12 is a diagram illustrating a manufacturing process of the disposable diaper according to the present invention.

A manufacturing method of an underwear-type disposable diaper 50, which is an absorbent article, is described hereinafter with reference to FIG. 12. FIG. 12 is a diagram illustrating a manufacturing process of the disposable diaper 50, where a surface on the skin noncontacting side of the disposable diaper 50 is considered to be a front surface, and a surface thereof on the skin contacting side is considered to be a back surface.

First, a stretchable nonwoven fabric 2 serving as a crotch-side sheet 72 is bonded to a predetermined position with hot-melt adhesive on a surface on the skin noncontacting side of the disposable diaper 50 of a base sheet 71 serving as a nonstretchable nonwoven fabric (FIG. 12 (A)). The stretchable nonwoven fabric 2 is bonded in a state of being cut to a predetermined size, and is extended by 1.9 times, for example. Here, the stretchable nonwoven fabric 2 may be bonded to the nonstretchable sheet 74 arranged as reinforcement at an end of a front body portion 55 or a rear body portion 56, by a hot melt adhesive. Furthermore, sheets for forming a front waist gather 57 and a rear waist gather 58 are bonded to the front body portion 55 and the rear body portion 56 with hot-melt adhesive, respectively (FIG. 12 (B)).

On the other hand, as shown in FIG. 12 (C), the stretchable nonwoven fabric 2 is cut in a width direction (WD) in a state of being extended by 1.8 times, for example, and a first sheathing sheet 73 (a) arranged on the front body side and a second sheathing sheet 73 (b) arranged on the rear body side are further formed. The first sheathing sheet 73 (a) and the second sheathing sheet 73 (b) are arranged on the surface on the skin noncontacting side, that is on the side on which the crotch-side sheet 72 is arranged of the base sheet 71 with the shielding sheets respectively extended, and are bonded thereto with hot-melt adhesive (FIGS. 12 (D) and 12 (E)).

A back surface sheet 53 is arranged on a surface on the skin noncontacting side (a surface, on the same side as the side on which the crotch-side sheet 72 and the sheathing sheet 73 are arranged) of a chassis 54 thus formed (FIG. 12 (F)). A front surface sheet 51 and an absorbent core 52 are arranged on a surface on the skin contacting side (a surface on the side opposite to the side on which the back surface sheet 53 is arranged) of the chassis 54, and are bonded thereto with hot-melt adhesive or the like (FIG. 12 (G)). In order to form leg openings 60, U-shaped cuts 59 are respectively cut out with a cutter so as to be recessed toward the inside of the chassis 54 in side parts of the chassis 54 (FIG. 12 (H)). Furthermore, the front body portion 55 or the rear body portion 56 is folded toward the skin contacting side so that both side portions of the front body portion 55 and both side portions of the rear body portion 56 are respectively joined to each other to form a shape of underwear, thereby forming the underwear-type disposable diaper 50 (not shown). It should be noted that, although the first sheathing sheet 73 (a) and the second sheathing sheet 73 (b) are described to be bonded to the base sheet 71 after being respectively cut, the disposable diaper 50 may also be formed by: bonding the first sheathing sheet 73 (a) and the second sheathing sheet 73 (b) to the base sheet 71 in a continuous state; forming the cuts 59; bonding the absorbent core 52 or the like thereto; joining the front body portion 55 with the rear body portion 56 at the joining portions 63, respectively, in a state of being folded in half toward the skin contacting side; and finally separating from each other in the shape of underwear.

In the present embodiment, although a description is provided for a disposable diaper having the waist opening 61 and the pair of leg openings 60 by joining the front body portion 55 and the rear body portion 56 to each other at the predetermined joining portions 63, and formed in the shape of underwear, as shown in FIGS. 10 and 11, the present invention is not limited thereto. For example, the present invention may be used for an unfolded-type disposable diaper that can be worn by locking a front body portion 55 and a rear body portion 56 using a locking member or the like. Alternatively, the present invention may be used for a disposable diaper formed in the shape of underwear, which is locked by a locking member such as a re-lockable surface fastener, as used for the unfolded-type disposable diaper, at predetermined joining portions 63 of a front body portion 55 and a rear body portion 56, and is easily unlocked, and can be folded and relocked.

Furthermore, in the present embodiment, the crotch-side sheets 72 and leakage-prevention walls formed of a leakage-prevention sheet, i.e. leg gathers (not shown), may be respectively arranged along both ends in the width direction (WD) of the absorbent core 52 in the disposable diaper. More specifically, the leakage-prevention sheet may be provided so as to project in the width direction (WD) of the absorbent core 52 from a region between the absorbent core 52 and the chassis 54 or the back surface sheet 53, and at least one crotch-side sheet 72 may be arranged at an end in the width direction (WD) of the leakage-prevention sheet and fixed thereto with hot-melt adhesive or the like. The leakage-prevention sheet may remain projecting in the width direction (WD) of the absorbent core 52. Alternatively, the leakage-prevention sheet may be folded toward the center in the width direction (WD) of the absorbent core 52 so that its folded portion is arranged on a surface on the skin contacting side of the absorbent core 52.

Although the back surface sheet 53 is arranged on an outermost surface of the chassis 54, the present invention is not limited thereto and, for example, the back surface sheet 53 may be provided between the absorbent core 52 and the chassis 54. Alternatively, when the chassis 54 is formed of a plurality of sheets, the back surface sheet 53 may be provided between the sheets.

In the present invention, although the crotch-side sheets 72 and the sheathing sheet 73 that impart stretch properties throughout are bonded to the base sheet 71 in respectively extended states to form the composite sheet 1 that has developed stretch properties, the present invention is not limited thereto. For example, the sheathing sheet 73 that has partially developed stretch properties by being subjected to gear-stretch processing may be bonded to the base sheet 71. Furthermore, the number of times of gear-stretch processing is not limited to one. Gear-stretch processing may be performed twice in different directions, as described above, to form a stretchable nonwoven fabric 2 that has developed stretch properties in the longitudinal direction (direction C) and the transverse direction (direction M). Furthermore, the stretchable nonwoven fabric 2 or the nonstretchable nonwoven fabric 3 to be bonded is not limited to a single layer, and may have a plurality of layers overlapped with and bonded to one another. This allows the strength of the composite sheet 1 to be formed high.

In the present embodiment, although the composite sheet 1 is described as an underwear-type disposable diaper, the composite sheet 1 can be also employed in other products. For example, the composite sheet can be employed as a side stretchable sheet of a side-flap or side-stretchable underwear-type diaper in an absorbent article of a taping type, a wing for fixing to underwear in a napkin, a stretchable member such as a cuff of a disposable surgical gown, an ear band of a disposable mask, a disposable bandage, a surface material of fomentations, and so on.

EXAMPLES

While preferred embodiments of the present invention have been described and illustrated above, it is to be understood that they are exemplary of the invention and are not to be considered to be limiting. It should be noted that, as used herein, the direction MD corresponds to the lateral direction (direction M) in the abovementioned embodiment (FIGS. 1, 5 and the like), and is a so-called machine direction. On the other hand, the CD direction corresponds to the longitudinal direction (direction C) in the abovementioned embodiment (FIGS. 1, 5 and the like), and is a so-called cross direction orthogonal to the machine direction.

A raw stretchable nonwoven fabric 5, in which the mixture ratio (ratio by weight) of polypropylene fiber (PP) to polyurethane fiber (TPU) was 55 to 45, was manufactured. The raw stretchable nonwoven fabric 5 was then subjected to gear-stretch processing using shaping rollers 10 and 10', thereby obtaining a stretchable nonwoven fabric 2. A basis weight of the raw stretchable nonwoven fabric 5 was 35 g/m$^2$.

Thereafter, the stretchable nonwoven fabric 2 in a state of being extended by 1.8 times in the machine direction (MD) was bonded to a nonstretchable nonwoven fabric 3 having a basis weight of 19 g/m$^2$, by way of a hot-melt adhesive. It should be noted that an adhesive 4 was applied to the nonstretchable nonwoven fabric 3 in a spiral coating pattern, and the basis weight thereof was 5 g/m$^2$.

As shown in Table 1, composite sheets were formed with the nonstretchable nonwoven fabric 3 having a fixed basis weight and the stretchable nonwoven fabric 2 having variable basis weights, and tested (on the left of the table, Examples 1 to 4). In addition, composite sheets were formed with the stretchable nonwoven fabric 2 having a fixed basis weight and the nonstretchable nonwoven fabric 3 having variable basis weights, and tested (on the right of the table, Examples 5 to 7).

TABLE 1

|  |  | Example 1 | Example 2 | Example 3 | Example 4 | Example 5 | Example 6 | Example 7 |
|---|---|---|---|---|---|---|---|---|
| Basis Weight of Nonstretchable nonwoven Fabric | g/m$^2$ | 19 | 19 | 19 | 19 | 19 | 25 | 30 |
| Basis Weight of Raw Stretchable Nonwoven Fabric | g/m$^2$ | 25 | 35 | 40 | 45 | 35 | 35 | 35 |
| Maximum Strength in Nonstretch Direction | N/50 mm | 28.4 | 26.6 | 27.6 | 29.1 | 30.2 | 33.4 | 41.0 |
| Tensile Strength with 60% Extension in Stretch Direction | N/50 mm | 3.47 | 4.19 | 5.03 | 6.12 | — | — | — |
| Basis Weight of Composite Sheet | g/m$^2$ | 70 | 86 | 92 | 103 | 68 | 78 | 85 |
| PP to TPU (Ratio by Weight) | — | 55 to 45 | 55 to 45 | 55 to 45 | 55 to 45 | 55 to 45 | 55 to 45 | 55 to 45 |

According to Table 1, regarding the composite sheets formed with the nonstretchable nonwoven fabric 3 having a fixed basis weight and the stretchable nonwoven fabric 2 having variable basis weights (on the left of the table), a tensile strength when being stretched to 60% extension in the stretch direction became greater as the basis weight of the stretchable nonwoven fabric 2 became greater, and a maximum strength (maximum breaking strength) in a nonstretch direction was not significantly changed. Alternatively, regarding the composite sheets formed with the stretchable nonwoven fabric 2 having a fixed basis weight and the nonstretchable nonwoven fabric 3 having variable basis weights (on the right of the table), the maximum strength in a nonstretch direction became greater as the basis weight of the nonstretchable nonwoven fabric 3 became greater. Therefore, the maximum strength in a nonstretch direction can be adjusted by changing the basis weight of the nonstretchable nonwoven fabric 3. It should be noted that the maximum strength in a nonstretch direction is a maximum strength in a nonstretch direction of the composite sheet 1. A measurement sample was 50 mm in the stretch direction and 150 mm in the nonstretch direction, and obtained from the composite sheet 1 that was extended to a maximum extension of the nonstretchable nonwoven fabric 3. The maximum breaking strength thereof was measured according to the abovementioned procedure.

In addition, Comparative Examples 1 to 4 were prepared with raw stretchable nonwoven fabrics having the following basis weights. A sample of 50 mm in the stretch direction and 150 mm in the CD direction was obtained and a maximum breaking strength was measured according to the abovementioned procedure. The CD direction is a direction affecting the strength in the nonstretch direction of the composite sheet 1 obtained by joining the stretchable nonwoven fabric 2 with the nonstretchable nonwoven fabric 3. Thereafter, an estimated maximum breaking strength in the CD direction in a case where the stretchable nonwoven fabric 2 was used singularly in a state of being extended by 1.8 times was obtained on the basis of the maximum breaking strength measured above. In addition, a sample of 150 mm in the stretch direction and 50 mm in the CD direction was obtained from the raw stretchable nonwoven fabric 5, and then the tensile strength thereof in an extended state to 60% extension was measured according to the abovementioned procedures.

TABLE 2

|  |  | Comparative Example 1 | Comparative Example 2 | Comparative Example 3 | Comparative Example 4 |
|---|---|---|---|---|---|
| Basis Weight of Raw Stretchable Nonwoven Fabric | g/m² | 25 | 40 | 45 | 80 |
| Maximum Breaking Strength in CD (Nonstretch Direction of Composite Sheet): Sample Obtained in Relaxed State | N/50 mm | 6.8 | 15.5 | 20.4 | 37.9 |
| Maximum Breaking Strength in CD with 1.8 Times Extension (Estimated) | N/50 mm | 3.8 | 8.6 | 11.3 | 21.1 |
| Tensile Strength with 60% Extension in Stretch Direction | N/50 mm | 1.13 | 2.74 | 3.6 | 7.9 |
| PP to TPU (Ratio by Weight) | — | 55 to 45 | 55 to 45 | 55 to 45 | 55 to 45 |

According to Table 2, the strength became greater by increasing the basis weight of the stretchable nonwoven fabric 2. However, in order to obtain a strength greater than 20 N/50 mm, which is required for the composite sheet 1, only by the stretchable nonwoven fabric 2, the basis weight of the stretchable nonwoven fabric 2 must be greater than 80 g/m² (Comparative Example 4). On the other hand, in a case where the stretchable nonwoven fabric 2 had a basis weight greater than 80 g/m², a tensile strength thereof in an extended state to 60% extension exceeded a preferable range (7 N/50 mm) (Comparative Example 2, 3, and 4). Therefore, the stretchable nonwoven fabric 2, in a case of being used singularly, is not preferable for use in an absorbent article, since the maximum breaking strength thereof and the tensile strength thereof in an extended state are not balanced, thereby increasing manufacturing cost.

The invention claimed is:

1. A composite sheet, comprising:
   a nonstretchable sheet including wrinkles;
   a stretchable nonwoven fabric including belt-shaped nondense regions extending in a first direction and dense regions extending in the first direction; and
   an adhesive portion that joins the nonstretchable sheet and the stretchable nonwoven fabric, the stretchable nonwoven fabric, is joined, while being extended, to the nonstretchable sheet to form the wrinkles,
   wherein
   the dense regions include first dense regions on a first side of the stretchable nonwoven fabric and second dense regions on a second side which is opposite to the first side and further from the nonstretchable sheet than the first side,
   the first and second dense regions are alternately arranged in a second direction that is orthogonal to the first direction,
   the nondense regions are arranged between adjacent first and second dense regions in the second direction, and
   a maximum breaking strength of the composite sheet in the first direction and the second direction is at least 20 N/50 mm.

2. The composite sheet according to claim 1, wherein: the stretchable nonwoven fabric includes stretched thermoplastic fibers and unstretched thermoplastic fibers, and the stretched thermoplastic fibers have an average fiber diameter smaller than that of the partially unstretched thermoplastic fibers.

3. The composite sheet according to claim 1, wherein the stretchable nonwoven fabric comprises thermoplastic fibers and stretchable elastomer fibers,
   wherein the nondense regions are stretchable in such a way that stretch of the elastomer fibers is allowed by stretching the thermoplastic fiber in a stretch processing and an elongated part of the nondense regions is used as an extension margin.

4. The composite sheet according to claim 1, wherein a basis weight of the stretchable nonwoven fabric in a nonextended state is 20 to 100 g/m².

5. The composite sheet according to claim 1, wherein a strength of the stretchable nonwoven fabric, in an extended state in the second direction to 75% extension, is no greater than 5 N/50 mm.

6. The composite sheet according to claim 1, wherein a basis weight of the nonstretchable sheet in an extended state is 10 to 50 g/m².

7. The composite sheet according to claim 1, wherein
a basis weight of the composite sheet in a nonextended state is no greater than 200 g/m², and
a basis weight of the composite sheet in an extended state to a natural length of the nonstretchable nonwoven fabric is no greater than 130 g/m².

8. The composite sheet according to claim 1, wherein a tensile strength of the composite sheet, in an extended state to 60% extension, is no greater than 7 N/50 mm.

9. An absorbent article, comprising: an absorbent core; and the composite sheet according to claim 1.

10. The composite sheet according to claim 1, wherein the wrinkles of the nonstretchable sheet extend in the first direction and spaced from each other in the second direction, and each of the wrinkles projects from the second side toward the first side.

11. The composite sheet according to claim 10, wherein the dense portions are compressed portions, the first dense portions on the first side are compressed from the second side toward the first side, and the second dense portions on the second side are compressed from the first side toward the second side.

12. The composite sheet according to claim 10, wherein the adhesive portion is intermittently arranged between the nonstretchable sheet and the stretchable nonwoven fabric and between adjacent winkles in the second direction.

13. An absorbent article having a longitudinal direction and a width direction that is perpendicular to the longitudinal direction, said absorbent article comprising:
a front body adapted to be positioned on a front side of a wearer's body;
a back body adapted to be positioned on a back side of the wearer's body;
an absorbent core having a substantially elongated shape, which is disposed along the longitudinal direction;
a nonstretchable sheet having wrinkles and a pair of U-shaped cutout portions that is project inward on both ends in the width direction;
a first stretchable nonwoven fabric disposed in the front body and in the back body on at least one of a skin contacting side and a skin noncontacting side opposite to the skin contacting side; and
a second stretchable nonwoven fabric disposed between the front body and back body on at least one of the skin contacting side and the skin noncontacting side,
wherein the first stretchable nonwoven fabric includes belt-shaped nondense regions extending in the longitudinal direction and belt-shaped dense regions extending in the longitudinal direction,
wherein
the dense regions include first dense regions on the skin contacting side and second dense regions on the skin noncontacting side and further from the nonstretchable sheet than the skin contacting side,
the first and second dense regions are alternately arranged in the width direction,
the nondense regions are arranged between adjacent first and second dense regions in the width direction,
wherein the second stretchable nonwoven fabric includes belt-shaped nondense regions extending in the longitudinal direction and belt-shaped dense regions extending in the longitudinal direction, the nondense regions and the dense regions being stretchable,
wherein
the dense regions include first dense regions on the skin contacting side and second dense regions on the skin noncontacting side and further from the nonstretchable sheet than the skin contacting side,
the first and second dense regions are alternately arranged in the width direction,
the nondense regions are arranged between first and second adjacent dense regions in the width direction,
wherein the first stretchable nonwoven fabric and the second stretchable nonwoven fabric are joined, in an extended state, to the nonstrechable sheet, and
wherein a maximum breaking strength, in the longitudinal direction and in the width direction, of a portion where the first stretchable nonwoven fabric and the nonstretchable sheet are joined with each other and of a portion where the second stretchable nonwoven fabric and the nonstretchable sheet are joined with each other is at least 20 N/50 mm.

* * * * *